United States Patent [19]

Gaviraghi

[11] Patent Number: 5,455,257
[45] Date of Patent: Oct. 3, 1995

[54] LACIDIPINE FOR THE TREATMENT OF ARTERIOSCLEROSIS

[75] Inventor: Giovanni Gaviraghi, Verona, Italy

[73] Assignee: Glaxo SpA, Verona, Italy

[21] Appl. No.: 94,150

[22] PCT Filed: Feb. 8, 1992

[86] PCT No.: PCT/EP92/00276

§ 371 Date: Aug. 11, 1993

§ 102(e) Date: Aug. 11, 1993

[87] PCT Pub. No.: WO92/14460

PCT Pub. Date: Sep. 3, 1992

[51] Int. Cl.$^6$ ................................................. A61K 31/44
[52] U.S. Cl. .................................................... 514/350
[58] Field of Search ................................................. 514/350

[56] References Cited

FOREIGN PATENT DOCUMENTS 2164336  3/1986  United Kingdom .

OTHER PUBLICATIONS

Triggle et al., *Drug News Perspect.*, vol. 4, No. 10, Dec. 1991, pp. 643–646.
Bernini et al., *Journal of Cardiovascular Pharmacology*, vol. 18, suppl 10, 1991, pp. S42–S45.
*Journal of Cardiovascular Pharmacology*, vol. 17, suppl. 4, 1991, pp. S94–S99.
Mason et al., *FASEB Journal*, vol. 6, No. 1, Jan. 1992, p. A399, abstract No. 2301.
Keogh et al., *Journal of Cardiovascular Pharmacology*, vol. 16, suppl 6, 1990, pp. S28–S35.
Weinstein et al., *The American Journal of Medicine*, vol. 86, suppl. 4A, 1989, pp. 27–32.

*Primary Examiner*—Raymond Henley, III
*Assistant Examiner*—Phyllis G. Spivack
*Attorney, Agent, or Firm*—Bacon & Thomas

[57] ABSTRACT

The invention relates to a method for the treatment of arteriosclerosis in a mammal which comprises administering to said mammal an effective amount of (E)-4-[2-[3-(1,1-dimethylethoxy)-3-oxo-1-propenyl]phenyl]-1,4-dihydro-2,6-dimethyl-3,5-pyridinedicarboxylic acid diethyl ester, lacidipine, as well as methods of treatment of arteriosclerosis which comprise administering to a mammal, especially a human, in need thereof, a pharmaceutical composition comprising lacidipine and a pharmaceutically acceptable carrier or excipient.

11 Claims, No Drawings

LACIDIPINE FOR THE TREATMENT OF ARTERIOSCLEROSIS

This application is a 371 of PCT/EP92/00276 filed Feb. 8, 1992.

This invention relates to the use of lacidipine in the treatment or prevention of arteriosclerosis.

UK Patent Application GB 2164336A describes a novel group of 1,4-dihydropyridine derivatives which reduce intracelluar calcium in concentration by limiting transmembranal calcium in influx and thus the compounds may be useful for the treatment of cardiovascular disorders such as hypertension, anginopectories, myocardial ischaemia, congestive heart failure, cerebral vascular and peripheral disorders. A particularly preferred compound is (E)-4-[2[3-(1,1-dimethylethoxy)-3-oxo-1-propenyl]phenyl]-1,4-dihydro-2,6-dimethyl-3,5-pyridinedicarboxylic acid diethyl ester, which now has the approved name lacidipine. This compound has been found to exhibit a particularly marked selectivity for inhibiting transmembrane calcium movement in vascular smooth muscle compared to activity on cardiac muscle. This vascular selectivity coupled with a particularly prolonged duration of action indicated that it should be especially useful as an antihypertensive agent and this has been confirmed by clinical studies.

We have now found that lacidipine possesses a useful anti arteriosclerotic activity in addition to the known action on vascular smooth muscle. The anti arteriosclerotic activity of lacidipine may be demonstrated in a number of standard tests. Thus for example lacidipine was found to significantly reduce cholesterol esterification in cultured mouse peritoneal macrophages. Lacidipine also significantly reduces plaque formation in a cholesterol-fed rabbit test.

The compound may therefore be useful for the treatment or prevention of atherosclerosis, hypertensive arteriosclerosis, Monckebergs arteriosclecrosis, hyperplastic arteriosclerosis and further cardiovascular disorders induced thereby or associated with arteriosclerosis such as angina pectoris, myocardial infarction hypertension, apoplexy, intermittent claudication, gangrene, arteriosclerosis of the aorta, arteriosclerotic aneurysms and arteriosclerosis of the renal arteries.

The invention therefore provides for the use of lacidipine in the treatment or prevention of arteriosclerosis in mammals. A further aspect of the invention provides for the use of lacidipine in the manufacture of a medicament for the treatment or prevention of arteriosclerosis in mammals.

In yet a further aspect of the invention there is provided a method for the treatment and or prevention of arteriosclerosis in mammals which comprises administering lacidipine to said mammal.

For the treatment and or prevention of arteriosclerosis and cardiovascular diseases induced thereby lacidipine may be formulated in a conventional manner with one or more pharmaceutical excipients and or carriers.

Thus a further aspect of the invention provides for a pharmaceutical composition for use in the prevention or treatment of arteriosclerosis which comprises lacidipine and one or more pharmaceutical excipients and or carriers formulated for oral, sublingual, transdermal parenteral or rectal administration.

For oral administration the pharmaceutical composition may take the form of for example tablets, which may be film or sugar coated, capsules, powders, granules, solutions including syrups, or suspensions prepared by conventional means with acceptable excipients. For sub lingual administration the composition may take the form of tablets or lozenges formulated in conventional manner.

For parenteral administration lacidipine may be given as a bolus injection or by continuous infusion. The compositions may take such forms as suspensions, solutions or emulsions in oily or aqueous vehicles and may contain formulatory agents such forms as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a vehicle.

A proposed daily dosage of lacidipine for the treatment of man is in the range of 0.001 to 50 mg for example 0.005 to 20 mg which may conveniently be administered in one or more doses. The precise dose employed will depend on the age and condition of the patient as well as the route of administration.

For oral use lacidipine is conveniently administered to the human patient at a dose in the range 0.01 to 50 mg more preferably 0.05 to 20 mg per day. For parenteral use the compound is conveniently administered at a dose in the range of 0.001 to 2 mg more preferably 0.05 to 0.5 mg per day.

For oral use lacidipine is preferably administered twice or more particularly once a day.

Examples of suitable pharmaceutical formulations for administration of lacidipine for use in the treatment and or prevention of arteriosclerosis include those specifically described in UK patent application GB2164336A, and its U.S. equivalent, U.S. Pat. No. 4,801,599 and which by way of reference are incorporated herein.

The ability of lacidipine to prevent plaque formation was determined using the cuff injury model in cholesterol fed rabbits. In this test plaque is deposited on the aortic surface of the cholesterol-fed rabbits. Rabbits also given lacidipine at a dose of 3 mg/kg/day showed a significant reduction (approximatley 20%) in the aortic surface area covered by plaque.

I claim:

1. A method for the treatment of arteriosclerosis in a mammal in need thereof which comprises administering an effective amount of (E)-4-[2-[3-(1,1-dimethylethoxy)-3-oxo-1-propenyl]phenyl]-1,4-dihydro-2,6-dimethyl-3,5-pyridinedicarboxylic acid diethyl ester to said mammal.

2. A method as claimed in claim 1 for the treatment of a human with atherosclerosis.

3. A method for the treatment of arteriosclerosis in a mammal which comprises administering to said mammal a pharmaceutical composition comprising an effective amount of (E)-4-[2-[3-(1,1-dimethylethoxy)-3-oxo-1-propenyl]phenyl]-1,4-dihydro-2,6-dimethyl-3,5-pyridinedicarboxylic acid diethyl ester and a pharmaceutically acceptable carrier or excipient.

4. A method as claimed in claim 3 wherein the pharmaceutical composition is in a form suitable for oral or parenteral administration.

5. A method as claimed in claim 3 wherein the mammal is a human.

6. A method as claimed in claim 5 wherein the pharmaceutical composition is in a form suitable for oral administration.

7. A method as claimed in claim 6 wherein the effective amount is 0.01 to 50 mg.

8. A method as claimed in claim 7 wherein the effective amount is 0.05 to 20 mg.

9. A method as claimed in claim 5 wherein the pharmaceutical composition is in a form suitable for parenteral administration.

10. A method as claimed in claim 9 wherein the effective amount is 0.001 to 2 mg.

11. A method as claimed in claim 10 wherein the effective amount is 0.05 to 0.5 mg.

* * * * *